(12) United States Patent
Kojima et al.

(10) Patent No.: US 6,245,820 B1
(45) Date of Patent: Jun. 12, 2001

(54) METHOD FOR TREATING MENIERE'S DISEASE

(75) Inventors: Jun Kojima; Shingo Yanagida, both of Tokyo; Takeshi Otani, Omiya, all of (JP)

(73) Assignee: Nikken Chemicals, Co., LTD, Tokyo (JP)

( * ) Notice: Subject to any disclaimer, the term of this patent is extended or adjusted under 35 U.S.C. 154(b) by 0 days.

(21) Appl. No.: 09/529,470

(22) PCT Filed: Oct. 12, 1998

(86) PCT No.: PCT/JP98/04574

§ 371 Date: Apr. 14, 2000

§ 102(e) Date: Apr. 14, 2000

(87) PCT Pub. No.: WO99/20262

PCT Pub. Date: Apr. 29, 1999

(30) Foreign Application Priority Data

Oct. 16, 1997 (JP) .................................................. 9-297943
Sep. 17, 1998 (JP) ................................................ 10-262566

(51) Int. Cl.⁷ ................................................. A61K 31/045
(52) U.S. Cl. ............................................................ 514/738
(58) Field of Search ............................................. 514/738

(56) References Cited

U.S. PATENT DOCUMENTS 5,916,606 * 6/1999 Record et al. ............................ 426/3

FOREIGN PATENT DOCUMENTS 63-230627   9/1988   (JP) .
7-103017    7/1994   (JP) .
10-36255    2/1998   (JP) .

OTHER PUBLICATIONS

D. Yazawa, "Histopathological Study of Endolymphatic Hydrops", Jibi Rinsho 74, pp. 2450 to 2506 (1981).
M. M. Paparella et al, "Endolymphatic Hydrops and Otitis media", The Laryngoscope 89 pp. 43–58 (1979).

* cited by examiner

Primary Examiner—Theodore J. Criares
Assistant Examiner—Jennifer Kia
(74) Attorney, Agent, or Firm—Christie, Parker & Hale, LLP

(57) ABSTRACT

A medicine for the treatment of Meniere's disease containing, as an active ingredient, erythritol which is capable of significantly reducing the endolymphatic pressure by oral administration of a therapeutically effective amount of erythritol as an active substance.

6 Claims, 2 Drawing Sheets

METHOD FOR TREATING MENIERE'S DISEASE

DESCRIPTION

1. Technical Field

The present invention relates to a medicine for the treatment of Meniere's disease containing erythritol as an active ingredient.

2. Background Art

Meniere's disease is a disease of unknown cause, but it has been reported to be an endolymphatic hydrops by nature. It is believed that endolymphatic fluid accumulates due to excess production of endolymphatic fluid or due to disorders in absorption, whereby the endolymphatic hydrops is formed and the Reissner's membranes of the cochlear duct is risen and, as a result, symptoms such as ringing of the ears, hearing difficulties, dizziness, and a feeling of blocked ears are generated.

In the past, as a medicine for the treatment of Meniere's disease, the osmotic pressure diuretic medicine, Isosorbide (i.e., 1,4:3,6-dianhydro-D-sorbitol) has been used as an oral administration agent for the purpose of alleviating the endolymphatic hydrops. However, the osmotic pressure diuretic medicine, Isosorbide currently, which is clinically applied as a medicine for the treatment of Meniere's disease has difficulties in the viewpoint of taste. Further, it is a liquid, and therefore, there is the problem of inconvenience in the transportation.

DISCLOSURE OF THE INVENTION

Accordingly, an object of the present invention is to provide a medicine for the treatment of Meniere's disease which is superior in the viewpoint of taste, is capable of reducing the amount of the medicine to be administered by improving the type of formulation, and is easy to take by patients.

In accordance with the present invention, there is provided a medicine for the treatment of Meniere's disease comprising erythritol as an active ingredient.

BRIEF DESCRIPTION OF THE DRAWINGS

The present invention will now be explained in further detail with reference to the drawings.

In FIG. 1, D.W. is a symbol showing the distilled water administration group, * is a symbol showing the presence of a significant difference at the significant test of $p<0.05$, and ** shows a significant difference at the significant test of $p<0.01$.

BEST MODE FOR CARRYING OUT THE INVENTION

Figure 1:
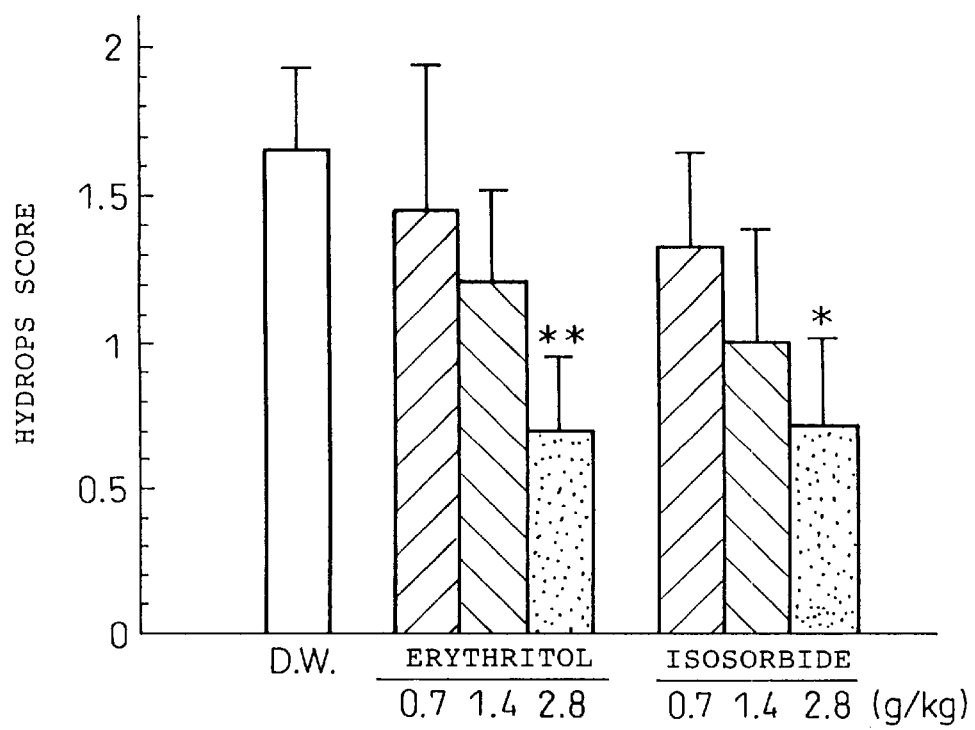
FIG. 1 is a view of the effect of alleviation of a hydrops with erythritol and Isosorbide in an endolymphatic hydrops model (an average value±standard error).

The present inventors engaged in various studies to find a medicine for the treatment of Meniere's disease superior to Isosorbide in viewpoint of taste and, as a result found that by intraduodenum administration of an erythritol aqueous solution, the endolymphatic pressure could be decreased quickly and found that, when using an aqueous erythritol solution as an oral agent, there is an equivalent effect as with isosorbide in viewpoint of dosage, whereby the present invention was completed.

According to the present invention, there is provided a medicine for the treatment of Meniere's disease having erythritol as an active ingredient. By orally ingesting a therapeutically effective amount of erythritol as an active ingredient, it is possible to significantly decrease the endolymphatic pressure.

The medicine for treatment of Meniere's disease according to the present invention is used in an amount, converted to erythritol, of normally 0.5 to 3 g/kg, preferably 0.8 to 1.5 g/kg, per kg body weight, and is taken one to three times a day depending on the symptoms.

Erythritol has the characteristics of having a refreshing sweet taste, being noncarious, and having zero calories, and therefore, is used in various confectioneries and beverages as a sweetener (or food ingredient). The toxicity thereof is extremely low. This is clear from the results of pilot acute toxicity tests using rats ($LD_{50}$ value (g/kg), oral administration: males 11.8, females 9.5, intravenous administration: males 6.1, females 5.4) (see Japanese Examined Patent Publication (Kokoku) No. 7-103017).

The medicine for treatment of Meniere's disease according to the present invention may be administered by all types of preparations as oral agents such as, for example, liquids, powders, granules, suspensions, tablets, capsules, dry syrups, etc. However, since the amount to be administered becomes large, powders, granules, and suspensions are preferable. In this way, in a preferable aspect of the present invention, the medicine for treatment of Meniere's disease according to the present invention is composed of erythritol as an active ingredient and, if desired, a base material. The concentration of the erythritol in the medicine composition is not particularly limited, but preferably is 90 to 100% by weight of the composition.

A suspension may be produced by adding and mixing to the erythritol, normally 0.1 to 10% by weight, preferably 0.2 to 1% by weight, per erythritol, of a suspension of one or more types of a suspending agent (or base material) selected from the group consisting of polyvinyl pyrrolidone, sodium carboxymethyl cellulose, carboxyvinyl polymer, hydroxypropyl cellulose, hydroxypropylmethyl cellulose, xanthane gum, gelatin, tragacanth gum, crystalline cellulose, alginate, agar, etc. Further, it is possible to add a flavor (e.g., 0.001 to 0.1% by weight) or a sweetener (e.g., 0.1 to 1% by weight) to the suspension to improve the ease of the administration.

A granular preparation may be produced by, for example, adding water, ethanol, or a mixed solution thereof etc. to erythritol, mixing them in a kneader, extruding the resultant mixture by the means of an extrusion granulator etc., drying the extrudate and sieving it after drying to obtain granules, then adding a small amount of Carbopol 971P ("trademark" for carboxyvinyl polymer made by B.F. Goodrich) and magnesium stearate etc. followed by mixing to obtain the granules. The granular preparation thus obtained can be ingested as it is or by suspension in a suitable amount of water.

A high density granular preparation can be produced, without using water, by mixing erythritol, a gum such as xanthane gum and tragacanth gum, and a lubricant such as calcium stearate and extruding the mixture under a high pressure, etc. The obtained high density granular preparation thus obtained may be administered as it is or after suspended in water.

The medicine for treatment of Meniere's disease according to the present invention may have suitably compounded thereinto, to an extent as long as the object of the present invention is not impaired, other medicinal ingredients, for example, a sympathetic nerve β-agonist, a vasodilative, or a cerebral circulation improving drug as a medicine having an action improving the circulation in the inner ear, a diuretic or adrenacortical steroid as a medicine for alleviating hydrolabyrinth, and a sedative, tranquilizer, antiemetic, antidizziness agent, or autonomic regulator as a medicine for sedation or control of nausea.

EXAMPLES

The present invention will now be explained in further detail to clarify the effects of the present invention with reference to pharmacological tests of the preparations and the Preparations Examples, but these are merely illustrations. The present invention is by no means limited thereto.

Test Example 1 (Endolymphatic Pressure Reducing Action)

Test Method
(Animals)
Guinea pigs (Hartley strain, body weights of 300 to 500 g) were used as groups each having 13 to 14 pigs.
(Test Medicines)
(1) Erythritol: The amounts of erythritol administered were three dosages of 0.7, 1.4, and 2.8 g/kg. These were dissolved in, and diluted with, distilled water to the administration volumes of 8 ml/kg.
(2) Isosorbide: The amounts of isosorbide administered as well were three dosages of 0.7, 1.4, and 2.8 g/kg. These were dissolved in, and diluted with, distilled water to the administration volumes of 8 ml/kg.
(Endolymphatic Sac Silver Nitrate Corrosion Method)
According to the method of Yazawa (Daishiro Yazawa, *Jibi Rinsho*, 74: 2450 to 2506 (1981)), a small amount (30 to 50 μl) of a 10% aqueous silver nitrate solution was surgically injected into the endolymphatic sac and, then, the incision sewn closed. Individuals after more than 21 days from the surgery were made to fast for at least 18 hours and, then, orally given the test medicine. One hour after the administration, the existence of urination was confirmed, then the animal was fixed under perfusion under anesthesia and the degree of hydrops in the cochlear duct was judged according to the criteria of Paparella (Paparella, M. M. et al.: *Laryngoscope*, 89:43–54 (1979) as:

None: 0, Slight: 1, Medium: 2, Severe: 3 The degree of advance of the eight Reissner's membranes in the cochlear duct which could be recognized as tissue sections was scored. The average was used as the result of the test of the individual.

Results
As a result of the test, the hydrops score of the distilled water administration group in the endolymphatic hydrops model was 1.66±0.27. For erythritol, a dosage-dependent reduction in the hydrops score due to oral administration of 0.7 g/kg, 1.4 g/kg, and 2.8 g/kg to 1.45±0.49, 1.21±0.31, 0.70±0.25 was recognized. In the 2.8 g/kg administration group, the hydrops score was significantly decreased compared with the distilled water administration group. For Isosorbide, a dosage-dependent decrease in the hydrops score due to oral administration of 0.7 g/kg, 1.4 g/kg, and 2.8 g/kg to 1.33±0.32, 1.01±0.38, and 0.72±0.30 was recognized. In the 2.8 g/kg group, the edema score was significantly decreased compared with the distilled water group.

FIG. 1 shows the results of the test for 0.7 g/kg, 1.4 g/kg, and 2.8 g/kg of erythritol and for 0.7 g/kg, 1.4 g/kg, and 2.8 g/kg of Isosorbide.

Test Example 2 (Endolymphatic Pressure Reducing Action)

Test Method
(Animals)
Guinea pigs (Hartley strain, body weights of 300 to 500 g) were used as groups each having three to five pigs.
(Test Medicines)
Erythritol: The amounts of erythritol administered were two dosages of 1.4 and 2.8 g/kg. These were dissolved in, and diluted with, distilled water to the administration volumes of 8 ml/kg.
(Endolymphatic Sac Silver Nitrate Corrosion Method and Endolymphatic Pressure Measurement Method)
According to the method of Yazawa (Daishiro Yazawa, *Jibi Rinsho*, 74: 2450 to 2506 (1981)), a small amount (30 to 50 μl) of a 10% aqueous silver nitrate solution was surgically injected into the endolymphatic sac and then the incision sewn closed. Individuals after more than 21 days from surgery were anesthetized and the respiratory tract secured, then a cannula was inserted into the duodenum and the test medicine injected.

The trunk was held in the prone position, the rear of the middle-ear cavity was cut open, and the cochlear duct was exposed. The cochlear basal rotatory tympanic wall or stria vascularis confirmed from the round window was cut open by a microdrill, then a glass capillary connected to a polyethylene tube was inserted into the basal rotatory cochlear duct using a micromanipulator and affixed air-tightly.

The inside of the closed circuit was filled, in advance, with endolymphatic equivalent solution, the polyethylene tube was connected to a pressure transducer, and the results recorded in a recticorder through an amplifier.

The test substance started to be administered after confirmation of the stability of the endolymphatic pressure.

Results
As a result of the above test, no change could be recognized in the endolymphatic pressure of the distilled water group. A dosage-dependent fall in the endolymphatic pressure due to the administration of 1.4 g/kg and 2.8 g/kg of erythritol into the duodenum was observed. In both the 1.4 g/kg group and the 2.8 g/kg group, the endolymphatic pressure was significantly decreased, compared with the distilled water group.

Figure 2:
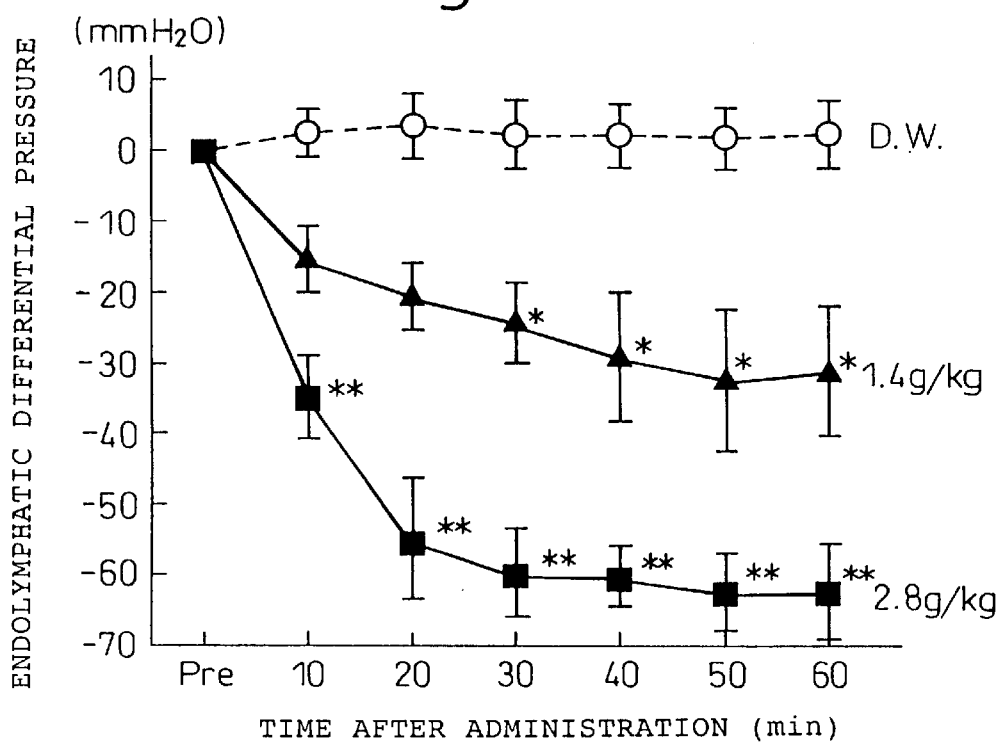
FIG. 2 is a view of the action of erythritol in decreasing the endolymphatic pressure (endolymphatic differential pressure) for an endolymphatic hydrops model (an average value±standard error). In the Figure, D.W. is a symbol showing the distilled water administration group, * is a symbol showing the presence of a significant difference test at $p<0.05$, and ** shows a significant difference at $p<0.01$.

FIG. 2 shows the results of tests using distilled water and 1.4 g/kg and 2.8 g/kg of erythritol.

Test Example 3 (Action Raising Plasma Osmotic Pressure)

Test Method
(Animals)
Guinea pigs (Hartley strain, body weights of 300 to 500 g) were used as groups each having five pigs.
(Test Medicine)
Erythritol: The amounts of erythritol administered were two dosages of 1.4 g/kg and 2.8 g/kg. These were dissolved in, and diluted with, distilled water to the administration volumes of 8 ml/kg.
(Method)
Normal guinea pigs were each anesthetized and their respiratory tracts secured, then a canular was inserted in the left carotid artery and used to sample blood. Further, a cannula was inserted into the duodenum and used to inject the test medicine. The trunk was held in the supine position and the blood was sampled before administration (pre). The blood was then sampled 15 minutes, 30 minutes, 60 minutes, 120 minutes, and 180 minutes after administration of the test substance. After sampling, to secure the amount of body fluid, physiological saline of the same amount as the blood sampled was injected from the blood sampling cannula. The sampled blood was separated by centrifugation, then the plasma was taken and the plasma osmotic pressure was measured using an osmotic pressure meter.

Results

As a result of the above test, no change could be recognized in the plasma osmotic pressure of the distilled water group. It was recognized by the administrations of 1.4 g/kg and 2.8 g/kg of erythritol that a dosage-dependent rise in the plasma osmotic pressure after 15 minutes from administration of the medicine into the duodenum peaked at 30 minutes and 60 minutes after administration. In particular, in the 2.8 g/kg erythritol group, a significant increase in the plasma osmotic pressure continued until 180 minutes after administration.

Figure 3:
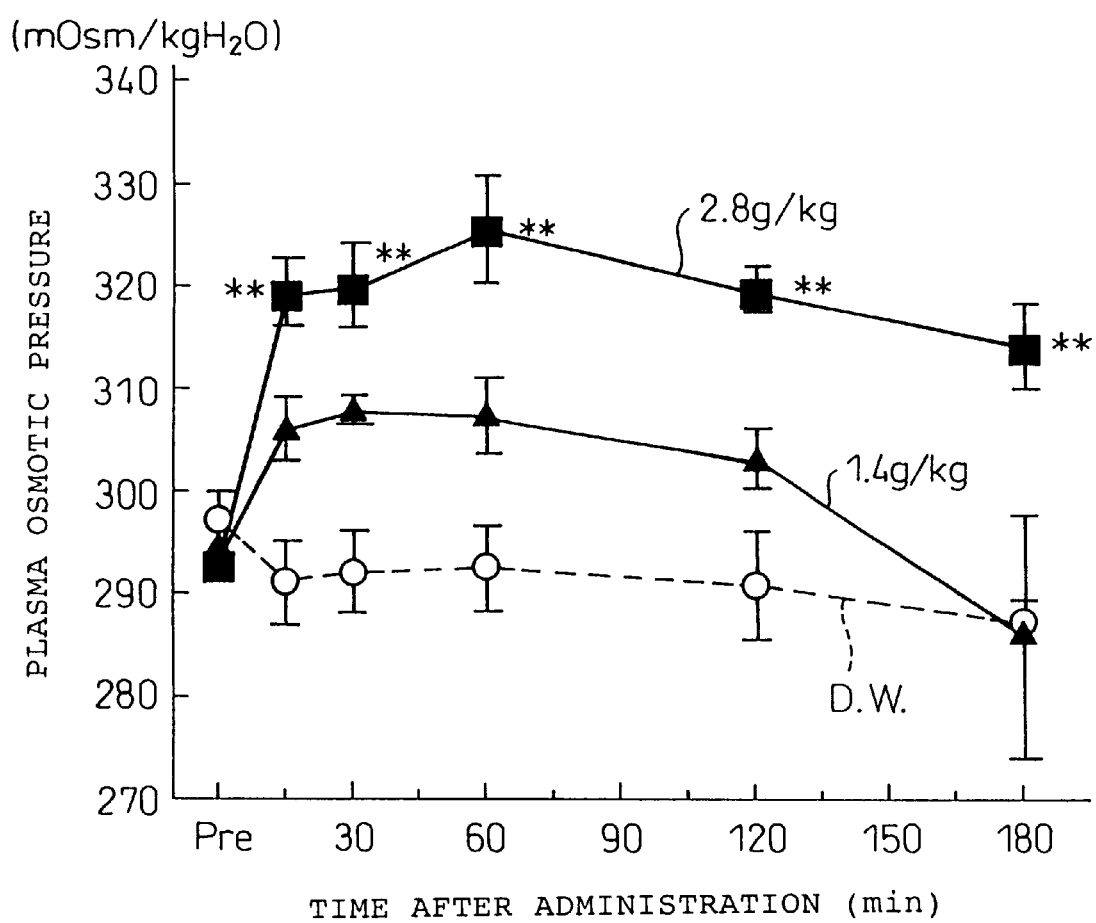
FIG. 3 is a view of the action of erythritol in increasing the plasma osmotic pressure in anesthetized guinea pigs (an average value±standard error). In the Figure, D.W. is a symbol showing the distilled water intraduodenum administration group, and ** is a symbol showing the presence of a significant difference at the signification test of $p<0.01$.

FIG. 3 shows the results of tests using distilled water and 1.4 g/kg and 2.8 g/kg of erythritol.

Example 1 (Suspension)

2 g of Carbopol 971P (trademark) and 2 g of citric acid were added to 200 g of erythritol. These were mixed in a mixer for 15 minutes to form a preparation, whereby a suspension capable of being suspended and taken at the time of use is produced. This preparation can be ingested by suspending a suitable amount (for example, packets corresponding to 10 g or 20 g of erythritol) in water at the time of use.

Example 2 (Granules)

20 g of water was added to 200 g of erythritol and mixed in a mixer. The mixture was mixed in a kneader, then dried at 60° C., then graded by 12 mesh and 16 mesh sieves. 2 g of Carbopol 971P (trademark) and 2 g of magnesium stearate were added to the granules thus obtained to form a granular preparation. The preparation can be ingested by suspending packets containing suitable amounts in water at the time of use.

Example 3 (High Density Granules)

A high density granular preparation was prepared without using water by extruding (1 mm diameter) 200 g of erythritol, 2 g of xanthane gum, and 2 g of calcium stearate using an extruder (Kurimoto Tekko). The preparation can be ingested by suspending packets containing suitable amounts in water at the time of use.

Example 4 (Preparation of Spherical Granules)

75 g of ethanol was added to 285 g of erythritol (100 mesh sieved product) and 15 g of anhydrous citric acid (100 mesh sieved product) and the mixture kneaded using a Shinagawa type universal mixer to prepare a paste. Next, this paste was extruded and granulated in a basket type granulator equipped with a 0.6 mm screen (die) to prepare crude granules. The crude granules thus obtained were transferred to a high speed mixing, agitating, and granulating device (high speed mixer FS-GS-10J, Fukae Kogyo K. K.) having a spherical granulating disk attached to the agitator and a granulating blade attached to a chopper. The device was operated for 30 seconds at a speed of 200 rpm of the agitator and 2000 rpm of the chopper to make the granules spherical. These were dried at 60° C. for 2 hours, then passed through a 14 mesh (1.18 mm) sieve and graded to a size remaining on a 42 mesh (0.35 mm) sieve to prepare a granular preparation (spherical granules).

INDUSTRIAL APPLICABILITY

The medicine for the treatment of Meniere's disease according to the present invention has the advantage of a much easier administration compared with isosorbide in terms of taste. Further, erythritol is noncarious and has zero calories, and therefore, there is the advantage that there is no concern over cavities or over administration of calories. Further, by formulating it as a powder, suspension, or granules, there is the advantage that less of an amount of the medicine should be administered compared with Isosorbide and the load on the patient can be lessened from this viewpoint as well.

What is claimed is:

1. A method for treating Meniere's disease comprising administering a pharmaceutical composition comprising a therapeutically effective amount of erythritol to a patient in need thereof.

2. The method according to claim 1, wherein the pharmaceutical composition is orally administered.

3. The method according to claim 1, wherein the erythritol is present in the pharmaceutical composition in an amount ranging from about 90% to about 100% by weight based on the total weight of the pharmaceutical composition.

4. The method according to claim 1, wherein the pharmaceutical composition further comprises a suspending agent.

5. The method according to claim 4, wherein the suspending agent is present in the pharmaceutical composition in an amount ranging from about 0.1% to about 10% by weight, based on the total weight of the pharmaceutical composition.

6. The method according to claim 4, wherein the suspending agent is selected from the group consisting of polyvinyl pyrrolidone, sodium carboxymethyl cellulose, carboxyvinyl polymer, hydroxylpropyl cellulose, hydroxypropylmetheyl cellulose, xanthane gum, gelatin, tragacanth gum, crystalline cellulose, alginate, and agar.

* * * * *